(12) United States Patent
Conrad et al.

(10) Patent No.: US 6,634,362 B2
(45) Date of Patent: *Oct. 21, 2003

(54) BRAIDED IMPLANT FOR SNORING TREATMENT

(75) Inventors: Timothy R. Conrad, Eden Prairie, MN (US); Mark B. Knudson, Shoreview, MN (US)

(73) Assignee: Restore Medical, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/036,915

(22) Filed: Jan. 3, 2002

(65) Prior Publication Data

US 2002/0056462 A1 May 16, 2002

Related U.S. Application Data

(63) Continuation of application No. 09/513,432, filed on Feb. 25, 2000, now Pat. No. 6,450,169, which is a continuation-in-part of application No. 09/434,653, filed on Nov. 5, 1999, now Pat. No. 6,401,717, which is a continuation-in-part of application No. 09/398,991, filed on Sep. 17, 1999, now Pat. No. 6,250,307.

(51) Int. Cl.$^7$ .............................................. A61B 19/00

(52) U.S. Cl. ..................................................... 128/897

(58) Field of Search ..................... 128/897–98; 600/12; 623/9, 11.11, 14.11

(56) References Cited

U.S. PATENT DOCUMENTS

| 3,998,209 A | 12/1976 | Macvaugh |
|---|---|---|
| 4,978,323 A | 12/1990 | Freedman |
| 5,046,512 A | 9/1991 | Murchie |
| 5,052,409 A | 10/1991 | Tepper |
| 5,133,354 A | 7/1992 | Kallok |
| 5,176,618 A | 1/1993 | Freedman |
| 5,178,156 A | 1/1993 | Takishima et al. |
| 5,190,053 A | 3/1993 | Meer |
| 5,281,219 A | 1/1994 | Kallok |
| 5,284,161 A | 2/1994 | Karell |
| 5,456,662 A | 10/1995 | Edwards et al. |
| 5,514,131 A | 5/1996 | Edwards et al. |
| 5,540,733 A | 7/1996 | Testerman et al. |
| 5,591,216 A | 1/1997 | Testerman et al. |
| 5,674,191 A | 10/1997 | Edwards et al. |
| 5,718,702 A | 2/1998 | Edwards |
| 5,792,067 A | 8/1998 | Karell |
| 5,843,021 A | 12/1998 | Edwards et al. |
| RE36,120 E | 3/1999 | Karell |
| 5,897,579 A | 4/1999 | Sanders |
| 5,922,006 A | 7/1999 | Sugerman |
| 6,250,307 B1 | 6/2001 | Conrad et al. |
| 6,450,169 B1 * | 9/2002 | Conrad et al. ............... 128/897 |

FOREIGN PATENT DOCUMENTS

| DE | 38 30 481 A1 | 3/1990 |
|---|---|---|
| DE | 200 15 980 U1 | 3/2001 |
| WO | WO 00/59398 | 10/2000 |

OTHER PUBLICATIONS

Boot, H. et al., "Long–Term Results of Uvulopalatopharyngoplasty for Obstructive Sleep Apnea Syndrome", *The Laryngoscope*, pp. 469–475 (Mar. 2000).

Cole, P. et al., "Snoring: A Review and a Reassessment", *The Journal of Otloaryngology*, vol. 24, No. 5, pp. 303–306 (1995).

(List continued on next page.)

*Primary Examiner*—John P. Lacyk
(74) *Attorney, Agent, or Firm*—Merchant & Gould P.C.

(57) ABSTRACT

A method and apparatus for treating snoring of a patient includes providing an implant for altering a dynamic response of a soft palate of the patient to airflow past the soft palate. The implant is embedded in the soft palate to alter the dynamic response. The implant has multiple fibers braided along a length of the implant.

10 Claims, 13 Drawing Sheets

OTHER PUBLICATIONS

Coleman, S. et al., "Midline Radiofrequency Tissue Reduction of the Palate for Bothersome Snoring and Sleep–Disordered Breathing: A Clinical Trial", *Otolaryngology–Head and Neck Surgery*, pp. 387–394 (Mar. 2000).

Dalmasso, F. et al., "Snoring: analysis, measurement, clinical implications and applications", *Eur. Respir. J.*, vol. 9, pp. 146–159 (1996).

Ellis, P. D. M. et al., "Surgical relief of snoring due to palatal flutter: a preliminary report", *Annals of the Royal College of Surgeons of England*, vol. 75, No. 4, pp. 286–290 (1993).

Fischer, Y. et al., "Die Radiofrequenzablation des weichen Gaumens (Somnoplastik)", *Redaktion*, pp. 33–40 (2000).

Harries, P.G. et al., "Review Article: The surgical treatment of snoring", *The Journal of Laryngology and Otology*, vol. 110, pp. 1105–1106 (Dec. 1996).

Huang, L., "Flutter of Cantilevered Plates in Axial Flow", *Journal of Fluids and Structures*, vol. 9, pp. 127–147 (1995).

Huang, L. et al., "Biomechanics of snoring", *Endeavour*, vol. 19, No. 3, pp. 96–100 (1995).

Kasey, K. et al., "Radiofrequency Volumetric Reduction of the Palate: An Extended Follow–Up Study", *Otolaryngology–Head and Neck Surgery*, vol. 122, No. 3, , pp. 410–414 (Mar. 2000).

LaFrentz, J.R.L. et al., "Palatal stiffening techniques for snoring in a novel canine model", *ARO Abstracts*, vol. 22, Abstrct No. 499, pp. 125–126 (Feb. 13–18, 1999).

Lorenz, C., "If he Snores—what can you do about it?", Today's Woman, Jul. 1948, p. 112.

Schwartz, R.S. et al., "Effects of electrical stimulation to the soft palate on snoring and obstructive sleep apnea", *J. Prosthet. Dent.*, vol. 76, No. 3, pp. 273–281 (1996).

Wiltfang, J. et al., "First results on daytime submadibular electrstimulation of suprahyoidal muscles to prevent nighttime hypopharyngeal collapse in obstructive sleep apnea syndrome", *Int. J. Oral Maxillofac. Surg.*, vol. 28, pp. 21–25 (1999).

Brochure, "Our Diagnostic Procedures are Snap®!", *Snap Laboratories*, 4 pgs.

Brochure, "Snore–Free Nights—Guaranteed!", *Your Health News*, 2 pgs.

Brochure, "Snoreless™", *Nutrition for Life International*, 2 pgs. (Dec. 1999).

Brochure, "Haven't you suffered Snoring long enough", *Somnoplasy*$^{SM}$, 2 pgs.

\* cited by examiner

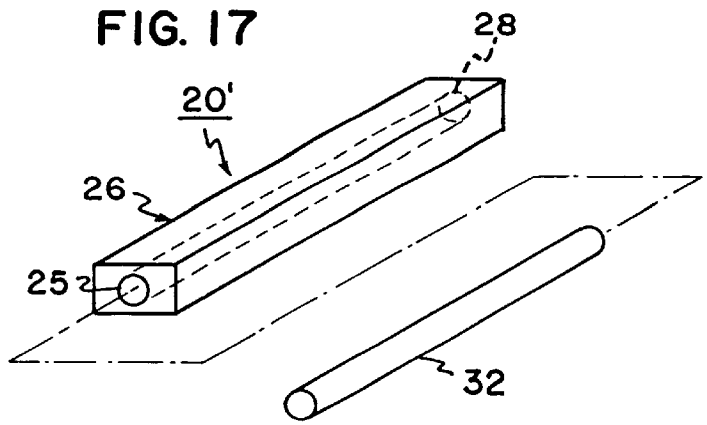
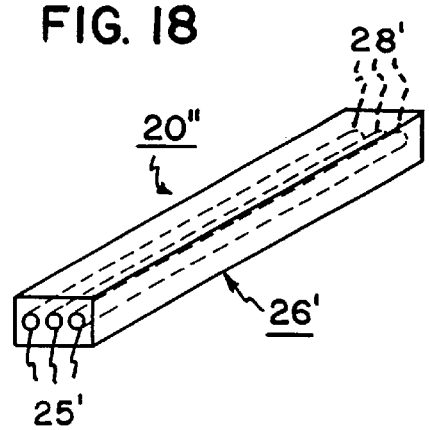
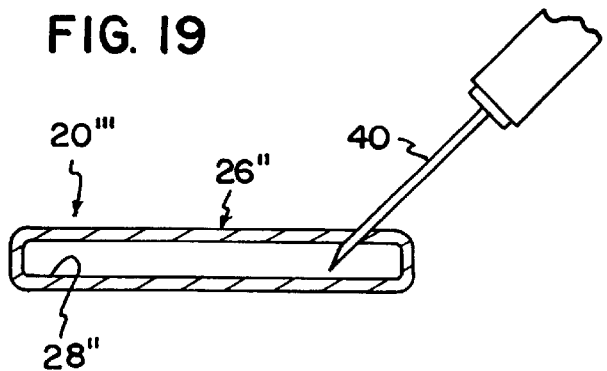

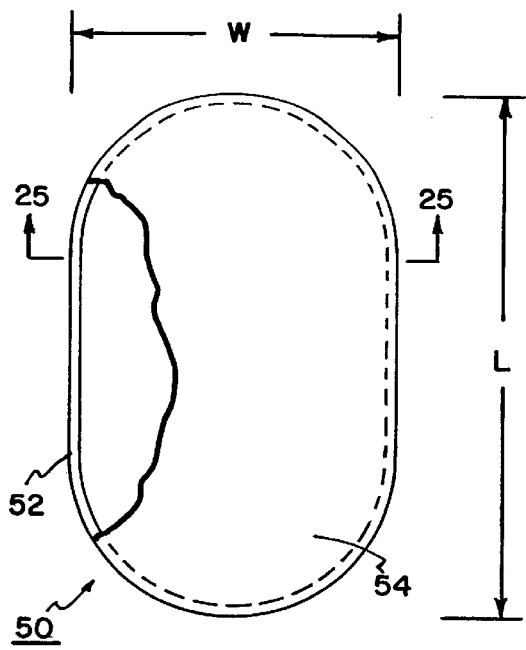
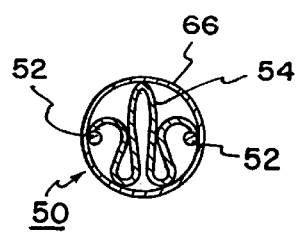
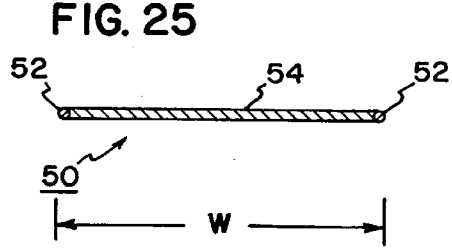
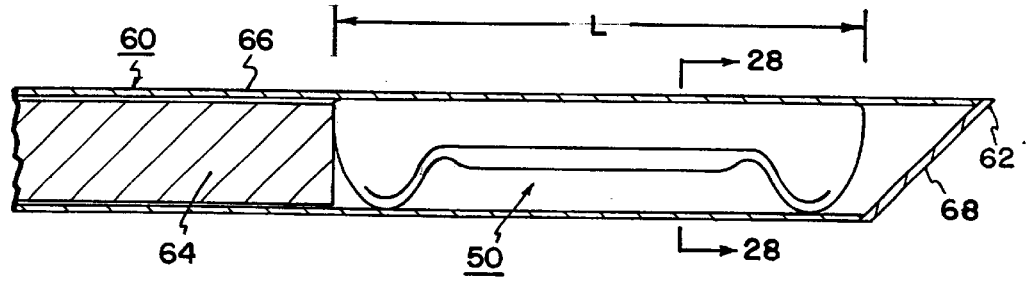
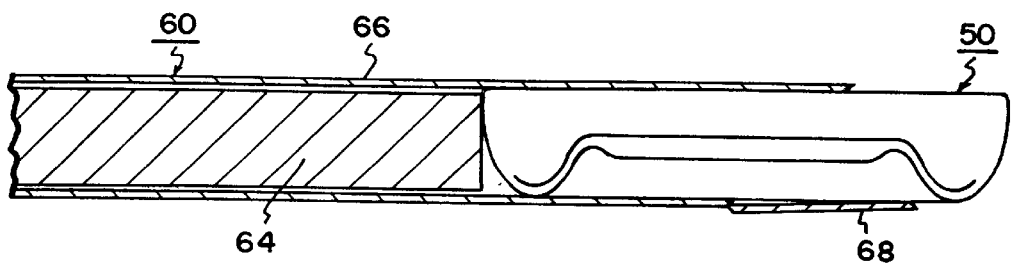

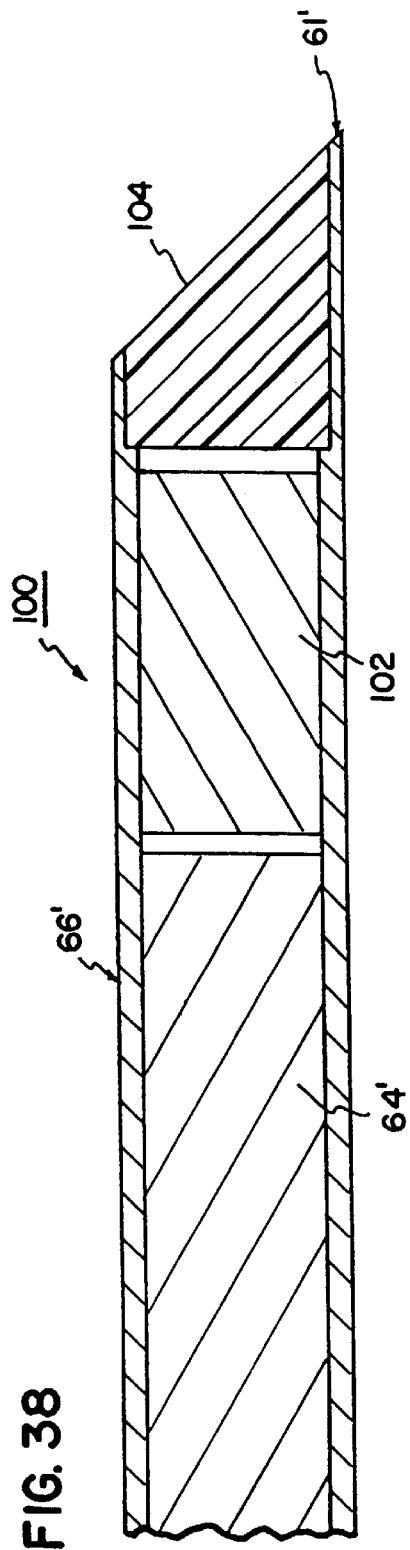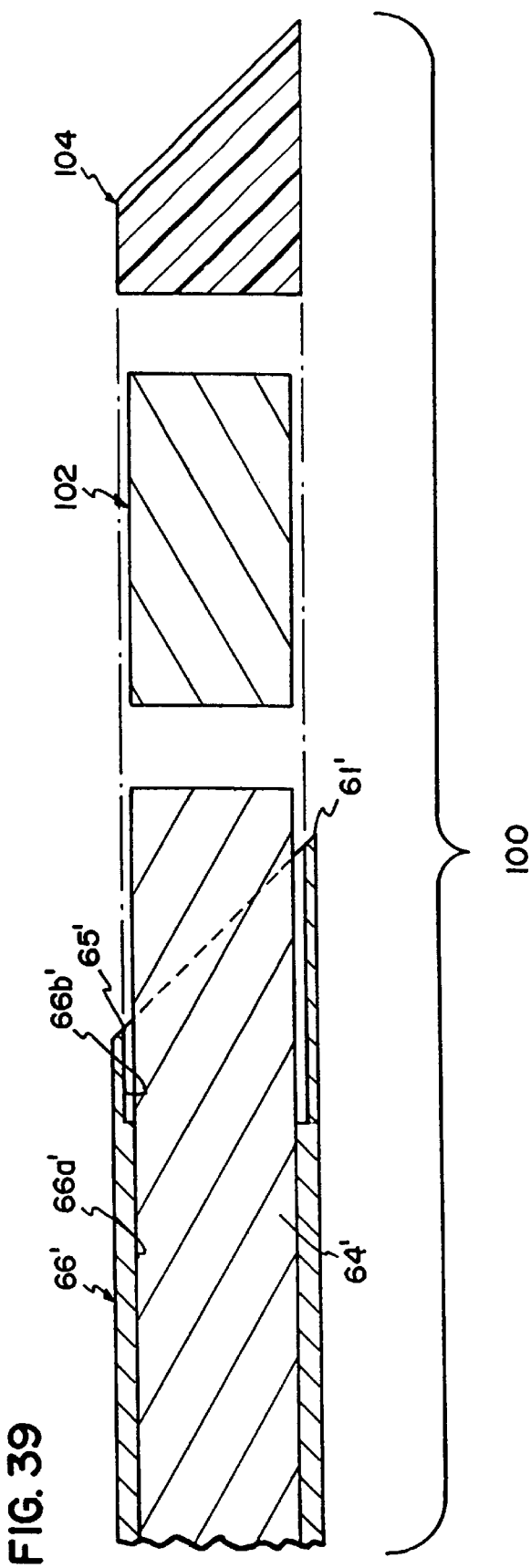

BRAIDED IMPLANT FOR SNORING TREATMENT

CROSS-REFERENCE TO RELATED APPLICATIONS

The present application is a continuation of U.S. patent application Ser. No. 09/513,432 filed on Feb. 25, 2000 now U.S. Pat. No. 6,450,169, which is a continuation-in-part of U.S. patent application Ser. No. 09/434,653 filed on Nov. 5, 1999 now U.S. Pat. No. 6,401,717, which is a continuation-in-part of U.S. patent application Ser. No. 09/398,991 filed Sep. 17, 1999 U.S. Pat. No. 6,250,307, all incorporated herein by reference and all filed in the name of joint inventors Timothy R. Conrad, Mark B. Knudson and Jerry C. Griffin.

BACKGROUND

1. Field of the Invention

This invention is directed to methods and apparatuses for treating snoring.

2. Description of the Prior Art

Snoring has received increased scientific and academic attention. One publication estimates that up to 20% of the adult population snores habitually. Huang, et al., "Biomechanics of Snoring", *Endeavour*, p. 96–100, Vol. 19, No. 3 (1995). Snoring can be a serious cause of marital discord. In addition, snoring can present a serious health risk to the snorer. In 10% of habitual snorers, collapse of the airway during sleep can lead to obstructive sleep apnea syndrome. Id.

Notwithstanding numerous efforts to address snoring, effective treatment of snoring has been elusive. Such treatment may include mouth guards or other appliances worn by the snorer during sleep. However, patients find such appliances uncomfortable and frequently discontinue use (presumably adding to marital stress).

Electrical stimulation of the soft palate has been suggested to treat snoring and obstructive sleep apnea. See, e.g., Schwartz, et al., "Effects of electrical stimulation to the soft palate on snoring and obstructive sleep apnea", *J. Prosthetic Dentistry*, pp. 273–281 (1996). Devices to apply such stimulation are described in U.S. Pat. Nos. 5,284,161 and 5,792,067. Such devices are appliances requiring patient adherence to a regimen of use as well as subjecting the patient to discomfort during sleep. Electrical stimulation to treat sleep apnea is discussed in Wiltfang, et al., "First results on daytime submandibular electrostimulation of suprahyoidal muscles to prevent night-time hypopharyngeal collapse in obstructive sleep apnea syndrome", *International Journal of Oral & Maxillofacial Surgery*, pp. 21–25 (1999).

Surgical treatments have been employed. One such treatment is uvulopalatopharyngoplasty. In this procedure, so-called laser ablation is used to remove about 2 cm of the trailing edge of the soft palate thereby reducing the soft palate's ability to flutter between the tongue and the pharyngeal wall of the throat. The procedure is frequently effective to abate snoring but is painful and frequently results in undesirable side effects. Namely, removal of the soft palate trailing edge comprises the soft palate's ability to seal off nasal passages during swallowing and speech. In an estimated 25% of uvulopalatopharyngoplasty patients, fluid escapes from the mouth into the nose while drinking. Huang, et al., supra at 99. Uvulopalatopharyngoplasty (UPPP) is also described in Harries, et al., "The Surgical treatment of snoring", *Journal of Laryngology and Otology*, pp. 1105–1106 (1996) which describes removal of up to 1.5 cm of the soft palate. Assessment of snoring treatment is discussed in Cole, et al., "Snoring: A review and a Reassessment", *Journal of Otolaryngology*, pp. 303–306 (1995).

Huang, et al., supra, describe the soft palate and palatal snoring as an oscillating system which responds to airflow over the soft palate. Resulting flutter of the soft palate (rapidly opening and closing air passages) is a dynamic response generating sounds associated with snoring. Huang, et al., propose an alternative to uvulopalatopharyngoplasty. The proposal includes using a surgical laser to create scar tissue on the surface of the soft palate. The scar is to reduce flexibility of the soft palate to reduce palatal flutter. Huang, et al., report initial results of complete or near-complete reduction in snoring and reduced side effects.

Surgical procedures such as uvulopalatopharyngoplasty and those proposed by Huang, et al., continue to have problems. The area of surgical treatment (i.e., removal of palatal tissue or scarring of palatal tissue) may be more than is necessary to treat the patient's condition. Surgical lasers are expensive. The proposed procedures are painful with drawn out and uncomfortable healing periods. The procedures have complications and side effects and variable efficacy (e.g., Huang, et al., report promising results in 75% of patients suggesting a full quarter of patients are not effectively treated after painful surgery). The procedures may involve lasting discomfort. For example, scar tissue on the soft palate may present a continuing irritant to the patient. Importantly, the procedures are not reversible in the event they happen to induce adverse side effects not justified by the benefits of the surgery.

SUMMARY OF THE INVENTION

According to one aspect of the present invention, methods and apparatuses are disclosed for treating snoring of a patient. The invention includes providing an implant for altering a dynamic response of a soft palate of the patient to airflow past the soft palate. The implant is embedded in the soft palate to alter the dynamic response. For example, the implant has a mass, stiffness or dampening sufficient to alter the dynamic response following the implantation without substantially impairing a function of the soft palate to close a nasal passage of the patient during swallowing.

According to another aspect of the present invention, the implant has multiple fibers braided along a length of the implant.

BRIEF DESCRIPTION OF THE DRAWINGS

FIG. 17 is an exploded perspective view of first modification of the implant of FIG. 13;

FIG. 18 is a perspective view of a modification of a housing of the embodiment of FIG. 17;

FIG. 19 is a side section view of a second modification of the implant of FIG. 13;

FIG. 24 is a top plan view, shown partially broken away, of a still further embodiment of the present invention;

FIG. 25 is a view taken along line 25—25 in FIG. 24;

FIG. 26 is a side sectional view of the implant of FIG. 24 collapsed and placed within a delivery tool;

FIG. 27 is the view of FIG. 26 with the implant in the process of being ejected from the delivery tool;

FIG. 28 is a view taken along line 28—28 in FIG. 26;

FIG. 38 is a side-sectional view of a delivery system for placing an implant in the soft palate;

FIG. 39 is the view of FIG. 38 following delivery of the implant from the delivery system;

DESCRIPTION OF THE PREFERRED EMBODIMENT

For ease of understanding the present invention, the dynamics of snoring are explained with reference to FIGS. 1–4. The hard palate HP overlies the tongue T and forms the roof of the mouth M. The hard palate HP includes a bone support B and does not materially deform during breathing. The soft palate SP is soft and is made up of mucous membrane, fibrous and muscle tissue extending rearward from the hard palate HP. A leading end LE of the soft palate SP is anchored to the trailing end of the hard palate HP. A trailing end TE of the soft palate SP is unattached. Since the soft palate SP is not structurally supported by bone or hard cartilage, the soft palate SP droops down from the plane of the hard palate HP in an arcuate geometry of repose.

The pharyngeal airway passes air from the mouth M and the nasal passages N into the trachea TR. The portion of the pharyngeal airway defined between opposing surfaces of the upper surface of the soft palate SP and the wall of the throat is the nasopharynx NP.

Figure 1:
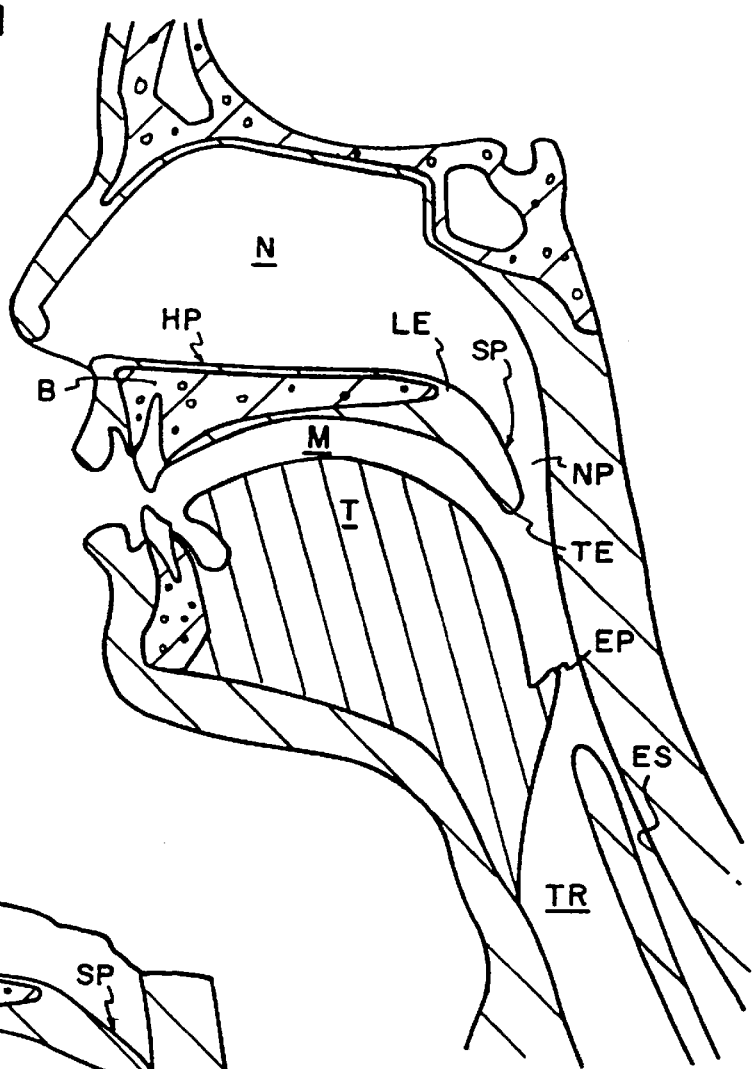
FIG. 1 is a side sectional view of a portion of a human head showing a soft palate in a relaxed state and in relation in adjacent anatomical features.

During normal breathing, the soft palate SP is in the relaxed state shown in FIG. 1 with the nasopharynx NP unobstructed and with air free to flow into the trachea TR from both the mouth M and the nostrils N.

Figure 2:
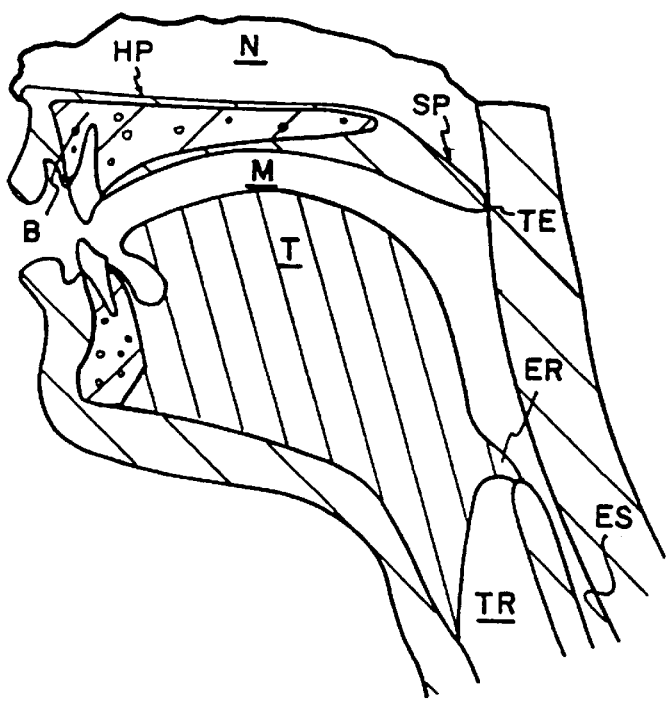
FIG. 2 is a portion of the view of FIG. 1 showing the soft palate in a flexed state.

During swallowing, the soft palate SP flexes and extends (as shown in FIG. 2) to close the nasopharynx NP thereby preventing fluid flow from the mouth M to the nasal passages N. Simultaneously, the epiglottis EP closes the trachea TR so that food and drink pass only into the esophagus ES and not the trachea TR. The soft palate SP is a valve to prevent regurgitation of food into the nose N. The soft palate SP also regulates airflow through the nose N while talking. Since the soft palate SP performs such important functions, prior art techniques for surgically altering the soft palate SP can compromise these functions.

The majority of snoring is caused by the soft palate SP flapping back and forth. If breathing is solely through the nose N with the mouth closed, the trailing edge TE of the soft palate SP is sucked into the nasopharyngeal space NP obstructing the airway and subsequently falls opening the airway in a repeating cycle. When the mouth is open, air flows over the upper and lower surfaces of the soft palate SP causing the soft palate SP to flap up and down alternating in obstructing the oral and nasal passageways M, N. The snoring sound is generated by impulses caused by rapid obstruction and opening of airways. Huang, et al., state the airway passage opening and closing occurs 50 times per second during a snore. Huang, et al., utilize a spring-mass model (FIG. 5) to illustrate oscillation of the soft palate in response to airflow (where the soft palate is the ball B of mass depending by a spring S from a fixed anchor A).

Figure 3:
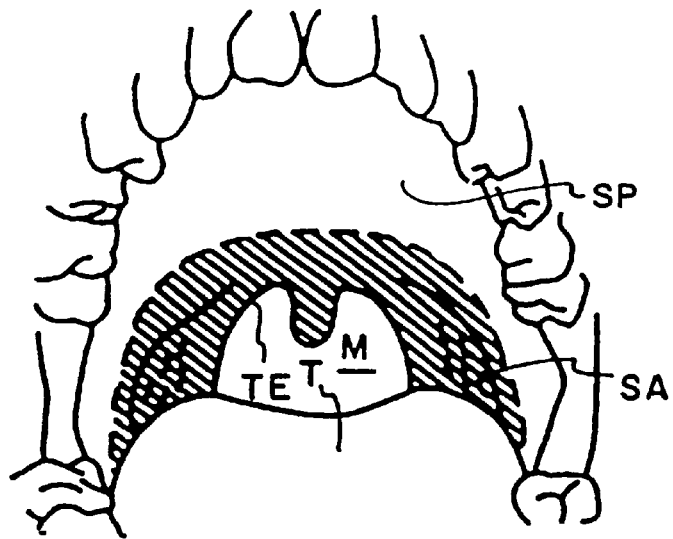
FIG. 3 is a front view of an interior of the mouth shown in FIG. 1 and showing an area to be ablated according to a first prior art surgical procedure.
Figure 4:
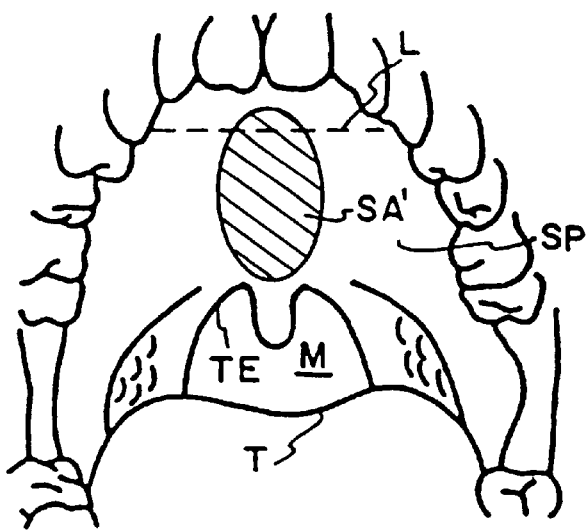
FIG. 4 is the view of FIG. 3 and showing an area to be scarred according to a second prior art surgical procedure.

Huang, et al., analogize the shortening of the soft palate SP in uvulopalatopharyngoplasty as effectively raising the critical air flow speed at which soft palate flutter will occur. The shaded area SA in FIG. 3 shows the area of the trailing end TE of the soft palate SP to be removed during this procedure. The alternative procedure proposed by Huang, et al., reduces the flexibility of the soft palate SP through surface scarring which is asserted as effecting the critical flow speed. The shaded area SA' in FIG. 4 shows the area to be scarred by this alternate procedure. In FIG. 4, dashed line L shows the demarcation between the soft and hard palates.

Figure 5:
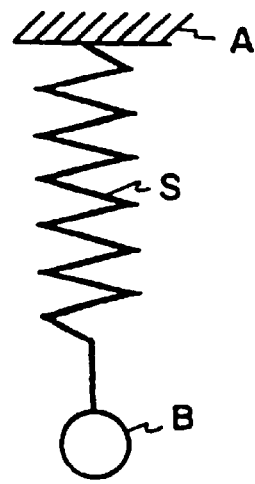
FIG. 5 is a schematic representation of a spring-mass system model of the soft palate.

Using the spring-mass model of FIG. 5 as a convenient model of the soft palate SP, the present invention is directed to a surgical implant into the soft palate SP to alter the elements of the model and thereby alter the dynamic response of the soft palate SP to airflow. The implant can alter the mass of the model (the ball B of FIG. 5), the spring constant of the spring S, the dampening of the spring S or any combination of these elements. Unlike the prior art surgical techniques, the implants that will be described are easy to insert in a small incision resulting in reduced patient discomfort and are not exposed to the interior of the mouth (such as the surface scarring of Huang, et al.) as a patient irritant. Also, as will be described, the degree of dynamic remodeling can be fine tuned avoiding the need for excessive anatomical modification and are reversible in the event of adverse consequences.

Figure 6:
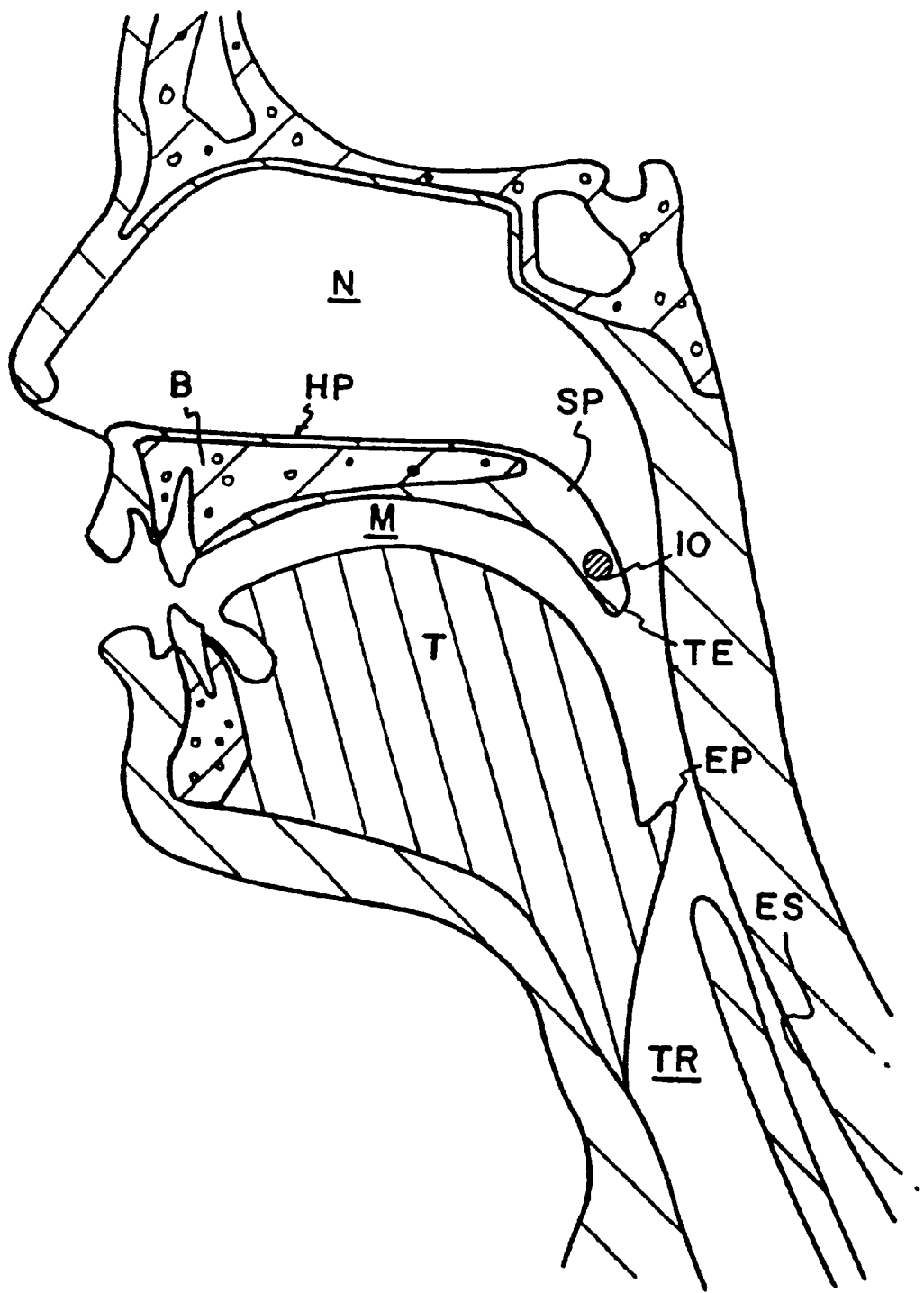
FIG. 6 is the view of FIG. 1 with the soft palate containing an implant according to a first embodiment of the present invention.
Figure 7:
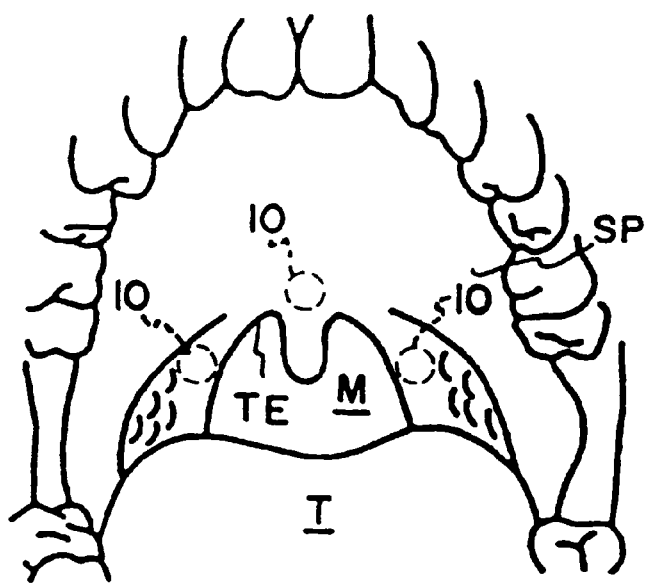
FIG. 7 is the view of FIG. 3 showing the embodiment of FIG. 6.
Figure 8:
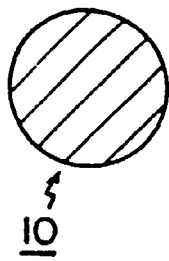
FIG. 8 is a cross-sectional view of the implant of FIG. 6.

FIGS. 6–7 illustrate a first embodiment of the present invention where individual units 10 of mass (in the form of implantable modular devices such as spheres or implants of other geometry) are imbedded in the soft palate SP in close proximity to the trailing end TE. With reference to the model of FIG. 5, the spheres add mass to the mass-spring system thereby altering dynamic response to airflow and adding resistance to displacement and accelerating. The placement of the units 10 of mass also alter the location of the soft palate's center of mass further altering the model and dynamic response.

The embodiment of FIGS. 6–10 is tunable to a particular patient in that multiple modules 10 can be implanted (as illustrated in FIG. 7). This permits the surgeon to progressively increase the number of implanted modules 10 until the altered dynamic response is such that snoring inducing oscillation is abated at normal airflow. The individual modules 10 may be placed into the soft palate SP through small individual incisions closed by sutures which is much less traumatic than the gross anatomical destruction of uvulopalatopharyngoplasty or the large surface area scarring proposed by Huang, et al.

Preferably, such modules 10 of mass are solid modules such as spheres of biocompatible material which are radiopaque (or radio-marked) and compatible with magnetic resonance imaging (MRI). Titanium is such a material. By way of non-limiting example, the modules 10 of mass may be about 2–4 mm in diameter. In the case of pure, non-sintered titanium, each such sphere 10 would add 0.15–1.22 gm of mass to the trailing end TE of the soft palate SP and contribute to re-modeling the mass distribution of the soft palate SP. An example of an alternative material is any biocompatible ceramic.

Figure 9:
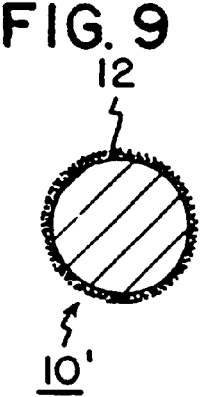
FIG. 9 is a first modification of the implant of FIG. 8 having a tissue in-growth layer.

As shown in FIG. 9, the spheres (labeled 10' to distinguish from the version 10 of FIG. 8) may be sintered throughout or otherwise provided with tissue growth inducing material 12 on their outer surface. Such material may be a sintered outer layer or a coating or covering such as a polyester fabric jacket. Such material permits and encourages tissue in-growth to secure the implant 10' in place. Also, placement of an implant 10 or 10' will induce a fibrotic response acting to stiffen the soft palate SP (and further alter the dynamic response and resistance to displacement and acceleration). A sintered or coated sphere 10' will enhance the fibrotic response and resulting stiffening.

Figure 10:
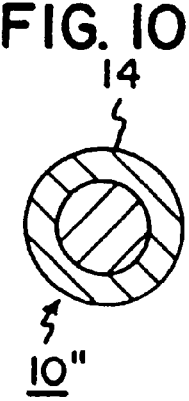
FIG. 10 is a second modification of the implant of FIG. 8 having a smooth outer layer.

While tissue in-growth and enhanced fibrotic response have the benefits described above, such embodiments may make the implant 10' more difficult to remove in the event reversal of the procedure is desired. Therefore, as shown in FIG. 10 as an alternative, the spheres (labeled 10" to distinguish from the implants 10, 10') may be coated with smooth coating 14 (such as parylene or PTFE) to reduce fibrosis.

The embodiments of FIGS. 6–10 add to and relocate the mass of the spring-mass system of FIG. 5 to remodel the dynamic response. The amount of mass is selected to alter the dynamic response but not preclude the soft palate SP being moved to close off nasal passages N during swallowing. Through fibrotic response and incision healing, the spring S of the model is stiffened.

In addition to modifying the mass profile of the spring-mass system, the spring component S of FIG. 5 can be modified (alone or in combination with mass modification) to alter dynamic response. FIGS. 11–16 illustrate an implant 20 in the form of a flexible strip for placement in the soft palate. The use of the term "strip" herein is not intended to be limited to long, narrow implants but can also include plates or other geometries implanted to alter the dynamic model of the soft palate SP. Elongated strips are presently anticipated as a preferred geometry to facilitate ease of implant.

Figure 11:
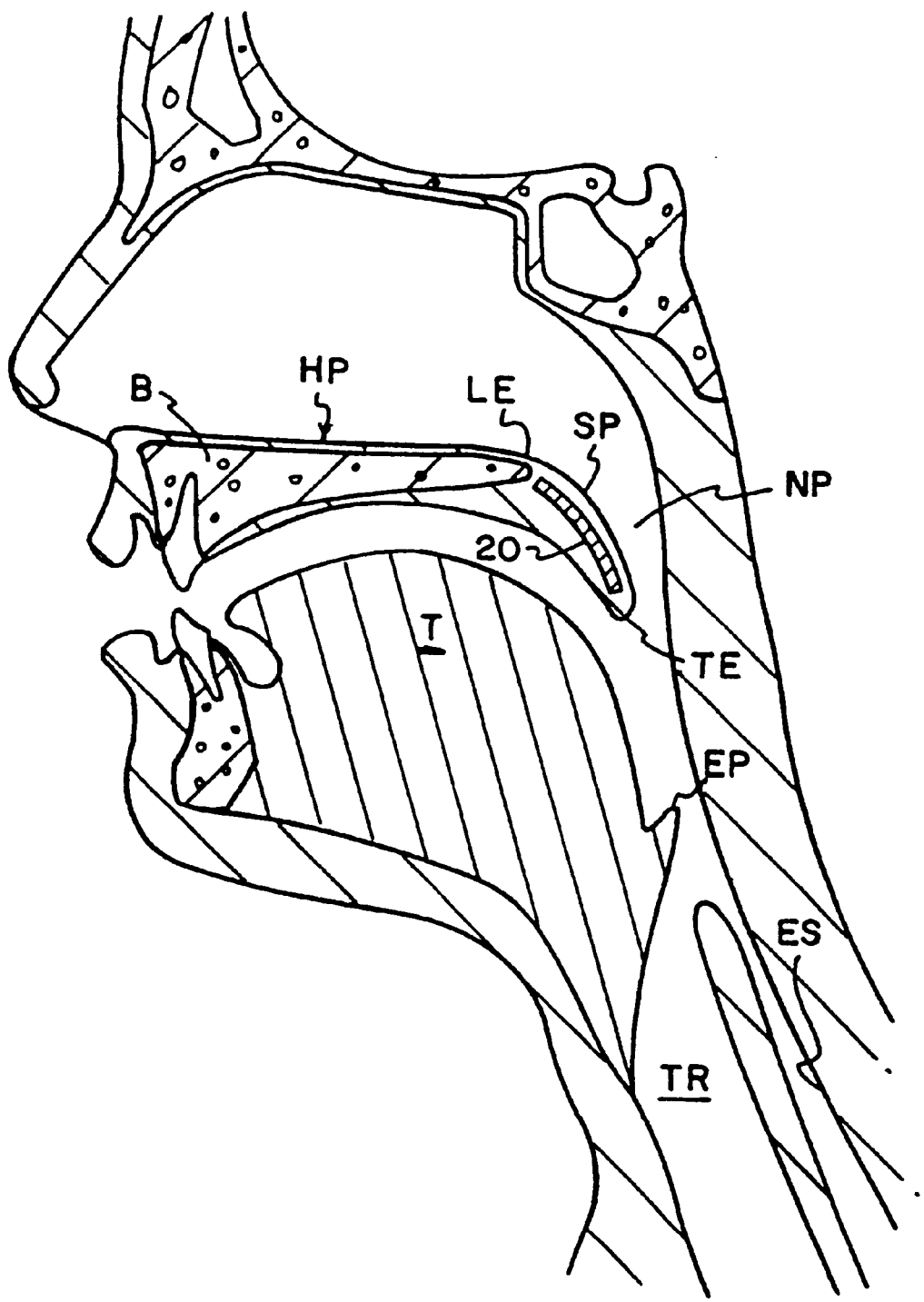
FIG. 11 is the view of FIG. 6 with the soft palate containing an implant according to a second embodiment of the present invention.
Figure 12:
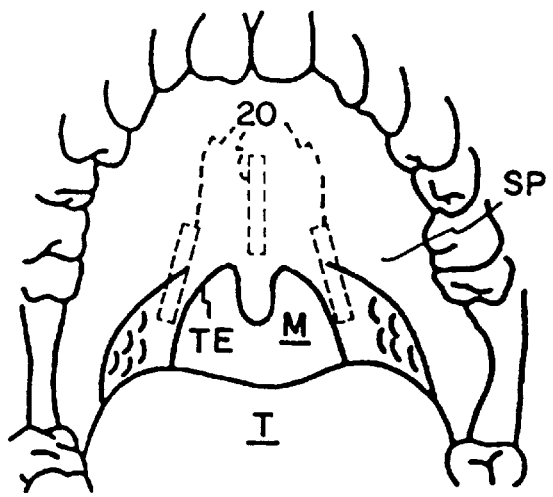
FIG. 12 is the view of FIG. 7 showing the embodiment of FIG. 11.

The strip 20 has a transverse dimension less than a longitudinal dimension. By way of non-limiting example, the strip may have a length $L_S$ of about 20–30 mm, a thickness $T_S$ of about 2–4 mm and a width $W_S$ of 5–10 mm. As shown in FIG. 11, the strip 20 is embedded in the soft palate SP with the longitudinal dimension Ls extending from adjacent the hard palate HP toward the trailing end TE of the soft palate SP. As shown in FIG. 12, multiple strips 20 may be embedded in the soft palate SP extending either straight rearward or angled to the sides while extending rearward. The strips 20 may be formed straight (FIG. 14) or pre-shaped (FIG. 15) to have a rest shape approximate to the side-cross section shape of the soft palate in a relaxed state.

Figure 16:
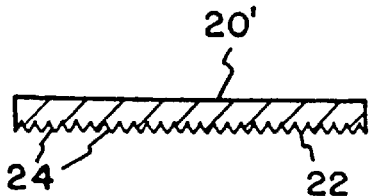
FIG. 16 is the view of FIG. 14 with the implant constructed to have greater flexion in a downward direction.
Figure 20:
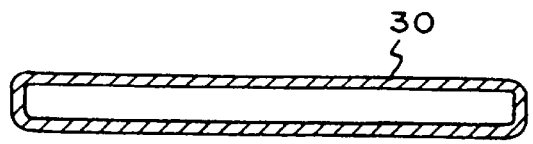
FIG. 20 is a cross-sectional view of an implant that is another embodiment of the present invention, the implant is shown in a flattened orientation.

The strips 20 may be any flexible, biocompatible material and are preferably radiopaque or radio-marked as well as MRI compatible. The strips 20 need not be elastic and having a material spring constant biasing them to their original shape. Such strips 20 could simply be flexible, plastically deformable strips which are stiffer than the soft palate SP to reinforce the soft palate SP and assist the soft palate SP in resisting deflection due to airflow. Such stiffening of the soft palate SP stiffens and dampens the spring S in the spring-mass system of FIG. 5 and alters the dynamic response of the soft palate SP. The strip 20 may be a spring having a spring constant to further resist deflection of the soft palate SP as well as urging the soft palate SP to the relaxed state of FIG. 5. The stiffness of the strip 20, a spring constant of the strip 20, and the number of strips 20, are selected to avoid preclusion of closure of the soft palate SP during swallowing. Examples of suitable materials include titanium and nitinol (a well-known nickel-titanium alloy). As with the examples of FIGS. 9 and 10, the strips 20 may be provided with tissue in-growth surfaces or may be coated as desired. Also, the strips may be structurally modified to control their flexibility. In FIG. 16, the bottom 22 of the strip 20 (facing the tongue after placement) is provided with transverse notches 24 to enhance downward flexion of the strip 20 relative to upward flexion of the strip 20 following placement.

Figure 13:
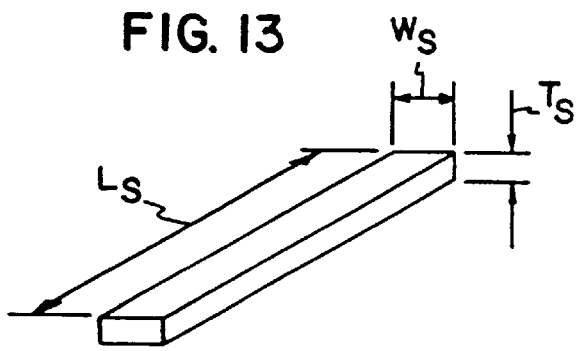
FIG. 13 is a perspective view of the implant of FIG. 11.
Figure 14:
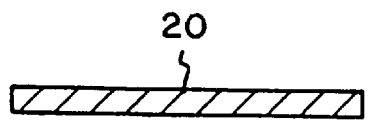
FIG. 14 is a cross-sectional view of the implant of FIG. 13.
Figure 15:
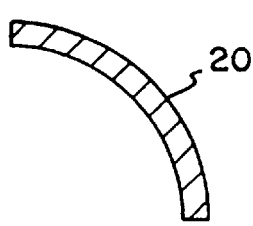
FIG. 15 is a view of the implant of FIG. 14 with the implant pre-formed to assume the shape of a soft palate in a relaxed state.

FIG. 17 provides an alternative to the strips 20 of FIG. 13. In FIG. 17, the strip 20' includes a housing 26 having an interior space 28 with an access opening 25. The interior space 28 extends in the longitudinal dimension of the housing 26. The strip 20' further includes a longitudinal insert 32 sized to be passed through the access opening 25 and into the space 28. By way of non-limiting example, the housing 26 could be silicone rubber (with radio-markers, not shown, to indicate placement) and the inserts 32 could be titanium rods or other flexible member. With the embodiment of FIG. 17, the housing 26 (without an insert) may be embedded in the soft palate SP. The housing 26 acts independently as a stiffening strip to add stiffness to the soft palate SP to alter the soft palate's dynamic response. In the event further stiffening or a spring action is desired, the implant 20' can be selectively tuned to the patient's unique dynamic model by placing the insert 32 into the space 28 at the time of initial surgery or during a subsequent procedure. The embodiment of FIG. 17, permits selection of an insert 32 from a wide variety of materials and construction so that an insert 32 of desired characteristics (e.g., stiffness and spring action) can be selected to be inserted in the space 28 and alter the dynamic response as desired. The embodiment of FIG. 17 also permits later removal of the insert 32 and replacement with a different insert 32 of different properties for post-surgery modification of the soft palate's dynamic response.

The embodiment of FIG. 18 is similar to that of FIG. 17. The housing 26' is provided with multiple, parallel-aligned interior spaces 28' and access openings 25'. In addition to the function and benefits of the embodiment of FIG. 17, the number of inserts 32 may be varied to alter and adjust the dynamic response of the soft palate SP.

FIG. 19 illustrates a still further embodiment of the strip implant. In FIG. 19, the strip 20''' is a bladder having a housing 26" in the form of a completely sealed envelope of flexible synthetic material defining an interior space 28". The envelope 26" is preferably self-sealing following needle injection. Fluid is injected into the housing 26" (e.g., through hypodermic needle 40 injection) to stiffen the strip 20'''. Addition of fluid further stiffens the strip 20''' and further alters the dynamic response of the soft palate SP. Removal of fluid increases the flexibility. Unlike the embodiments of FIG. 17 (where inserts 32 are most effectively replaced post-operatively through incision to alter flexibility), the embodiment of FIG. 19 permits selectively varying flexibility of the soft palate SP through needle injection. An alternative to FIG. 19 is to fill the space 28" with a so-called phase change polymer and inject a stiffening agent into the space 28" to alter the flexibility of the polymer.

FIGS. 20–23 illustrate a still further embodiment of the present invention. In the foregoing embodiments, the spring-mass system of FIG. 5 is altered by altering the mass of the soft palate SP or the spring characteristics of the soft palate SP. The dynamic response can also be altered by altering the force acting on the spring-mass system. Namely, the force acting on the soft palate SP is generated by airflow over the surface of the soft palate. The soft palate acts as an airfoil which generates lift in response to such airflow. By modifying the longitudinal (i.e., anterior to posterior) cross-sectional geometry of the soft palate SP, the aerodynamic response and, accordingly, the dynamic response are altered.

Figure 21:
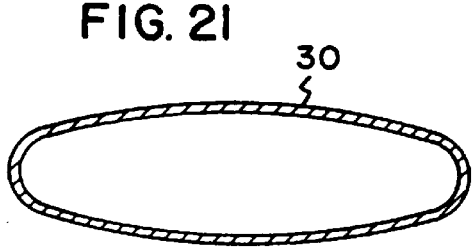
FIG. 21 is a cross-sectional view of the implant of FIG. 20 in an expanded orientation.
Figure 22:
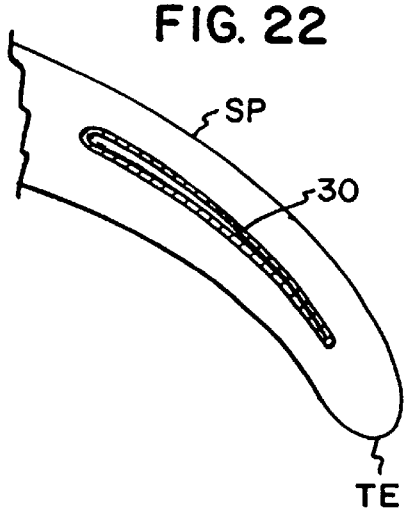
FIG. 22 shows the implant of FIG. 20 in the flattened orientation and implanted in the soft palate.
Figure 23:
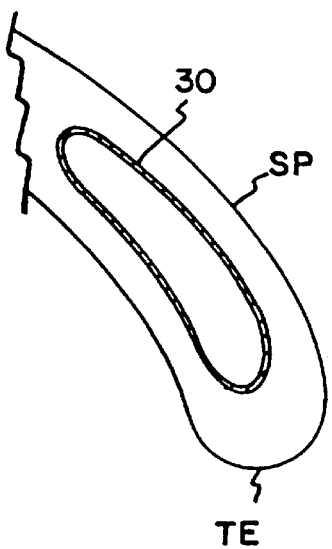
FIG. 23 shows the implant in FIG. 21 in the expanded orientation and implanted in the soft palate.

In the embodiments of FIGS. 20–23, the implant 30 is inserted into the soft palate SP through an incision. The implant 30 has an oval shape to cause deformation of the geometry of the soft palate SP. Prior to implantation, the implant 30 is preferably formed as a flat oval (FIGS. 20 and 22) for ease of insertion. After implantation, the implant 30 expands to an enlarged oval (FIG. 21 and 23). While such expansion could be accomplished mechanically (i.e., through balloon expansion), the implant 30 is preferably formed as a shape-memory alloy (such as nitinol) which expands to the enlarged shape in response to the warmth of the body. In addition to changing the aerodynamics of the soft palate SP, the implant 30 can be constructed with a mass and stiffness as desired to alter the spring and mass components of the spring-mass system of FIG. 5.

FIGS. 24–32 illustrate an expandable implant 50 and a delivery tool 60 for placing the implant 50 in the soft palate SP through a small incision. In FIGS. 24 and 25, the implant 50 is best illustrated as a flexible rim 52 with a fibrosis-inducing agent in the form of a flexible material, for example polyester fabric 54, retained on the rim 52. The rim 52 may be titanium or other material and resiliently biased to a rest geometry shown as an oval in FIG. 24 having a fully expanded width W and a length L. An oval is illustrated as a preferred geometry but other geometries may suffice. The geometries may include geometries selected to alter the shape of the soft palate SP. The polyester fabric 54 (such as Dacron® or the like) contains interstitial spaces for fibrosis and tissue integration to impart a stiffening to the soft palate SP.

The soft palate SP is schematically shown in FIGS. 29–32 with a palatal muscle PM extending distally from the bone B of the hard palate and surrounded by the soft tissue ST of the soft palate SP. The implant 50 is placed by compressing the implant 50 against the bias of the rim 52 into a compact cylindrical shape of length L and placing the compressed implant 50 in a distal end of a cylindrical delivery tool 60. The distal tip 62 of tool 60 is a blunt beveled end to follow an incision and to separate tissue as the tip 62 is advanced. A rod 64 is positioned proximal to the implant 50. The distal tip 62 is severable such that pushing rod 64 urges the implant 50 out of the distal tip 62. When removed from the delivery tool 60, the implant 50 springs back to an oval geometry.

Figure 29:
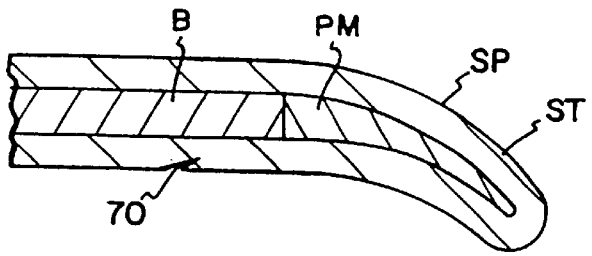
FIG. 29 is a side sectional view of the soft palate showing a palatal muscle in the soft palate.

The implant 50 is placed by forming a small incision 70 in the soft palate. In FIG. 29, the incision is made on the lower surface of the soft palate. The procedure could also be performed through the upper surface of the soft palate. The incision is sized to pass the distal tip 62 of tool 60 which is substantially smaller than the full width W of the expanded implant 50.

Figure 30:
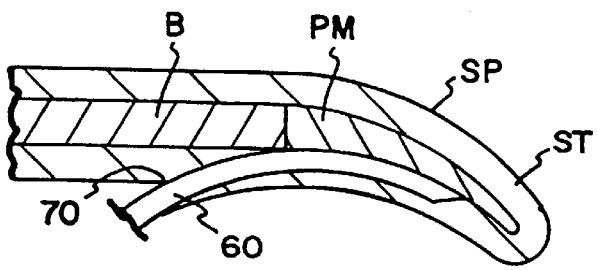
FIG. 30 is the view of FIG. 29 showing the delivery tool of FIG. 26 being advanced through an incision into the soft palate.
Figure 31:
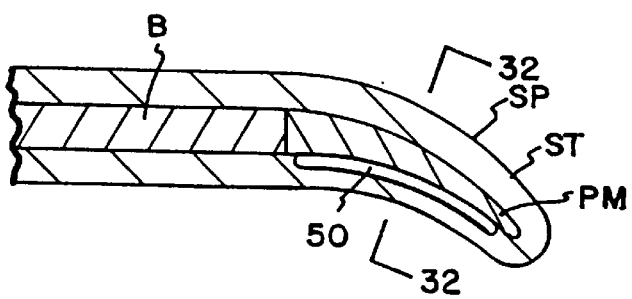
FIG. 31 is the view of FIG. 30 following delivery of the implant and removal of the delivery tool.
Figure 32:
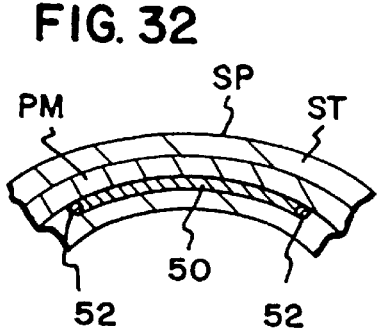
FIG. 32 is a view taken along line 32—32 in FIG. 31.
Figure 33:
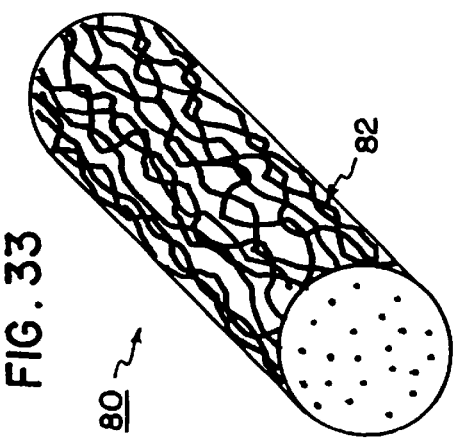
FIG. 33 is a perspective view of an implant according to a still further embodiment of the present invention showing only a bio-resorbable, first component.
Figure 34:
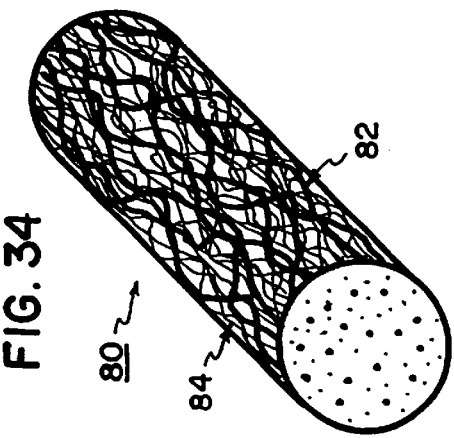
FIG. 34 is a perspective view of the implant of FIG. 33 showing both a first component and a second component.
Figure 35:
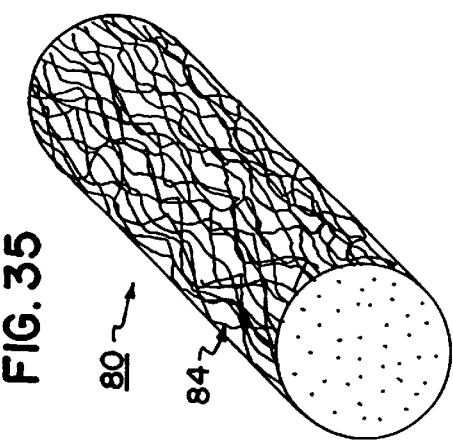
FIG. 35 is a perspective of the implant of FIG. 33 showing only the second component following bio-resorption of the first component.

Any suitable blunt dissecting tool may be inserted into incision 70 to separate the soft tissue ST from the palatal muscle PM by an amount sufficient to receive the expanded implant 50. The distal tip 62 is placed through the incision 70 and advanced through the soft palate SP with the distal tip 62 separating the soft tissue ST and the palatal muscle PM (FIG. 30). The tool 60 can be advanced by the physician tactilely noting position of the tool 60 or through any visualization technique (e.g., an endoscope on the distal tip 62). When the distal tip 62 is fully advanced, the outer tube 66 of tool 60 is retracted while holding rod 64 in place causing the implant 50 to be expelled through the distal tip 62. After full expulsion of the implant 50, tool 60 is removed through incision 70. The released implant 50 then expands into the oval shape and residing between the palatal muscle PM and the soft tissue ST (FIGS. 31 and 32).

In place, the fabric 54 of implant 50, encourages fibrosis and stiffening of the soft palate SP. By inserting a collapsed implant 50 through a small incision 70, a large surface area of fibrosis (and greater stiffening) can be achieved with a minimized incision 70 (resulting in reduced patient discomfort). Also, while the implant 50 is illustrated as being resiliently expandable, the implant 50 could expand or swell in response to other factors such as shape memory alloys (e.g., nitinol), smart polymers and balloon expandable and plastically deformable metals.

As an alternative to the foregoing, a catheter (not shown) can be passed through incision 70 and passed through the soft palate SP. The delivery tool 60 can be passed through the catheter. If desired, a coring tool (not shown) can be passed through the catheter to remove tissue from the soft palate SP prior to placing the implant 50 (or any implant of the previous embodiments). Also, for small implants, an implant can be placed through any short tube inserted into the soft palate through a needle poke and need not include a pre-incision.

With reference to FIGS. 33–36, a still further embodiment of the invention is described. In FIGS. 33–36, an implant 80 is shown having a cylindrical shape. The shape is illustrative only. The implant 80 may be deployed through a delivery tool 60 as previously described.

The implant 80 includes two stiffening components. A first component 82 is a base of a bio-resorbable material such as bio-resorbable suture formed into a woven cylindrical shape. Such material has a stiffness greater than soft tissue and is absorbed into the body over time. An example of such material is synthetic absorbable suture such as polydioxanone suture sold by Ethicon, Inc. under the trademark PDS II. Alternative materials could include absorbable bio-adhesives. A first component as described provides immediate post-operative stiffening to reduce or eliminate snoring immediately following placement of the implant 80 in the soft palate.

The second component 84 is any fibrosis inducing material combined with the first component 82. By way of non-limiting example, the second component may be filaments of polyester or polyester fabric (such as Dacron®) intertwined in the interstitial spaces of the first component 82. The presence of the second component 84 in the soft tissue of the soft palate SP induces fibrosis which stiffens the soft palate to reduce or eliminate snoring. The stiffening increases with time following implantation until the fibrotic response is steady state. The polyester second component 84 is permanent and does not bio-resorb. Therefore, the fibrosis effect (and, hence, the snoring reducing stiffening) remains permanently following implantation and following complete absorption of the first component 82.

Figure 36:
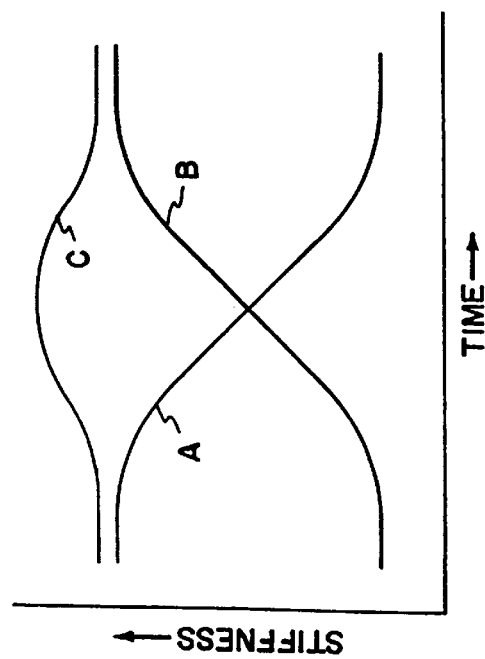
FIG. 36 is a graph showing decrease of palatal stiffening attributable to the first component and increase of palatal stiffening attributable to the first component.

The first component 82 and the second component 84 cooperate for the implant 80 to provide effective stiffening immediately post-operatively and chronically thereafter. The first component has a stiff material which stiffens the soft palate SP upon placement. However, over time, the first component is absorbed and the stiffening influence reduces and is eliminated. The second component 84 is formed of very floppy material which does not materially stiffen the soft palate immediately upon implantation of implant 10. However, with time, fibrosis induced by the material of the second component 84 stiffens the soft palate. This phenomena is illustrated in the graph of FIG. 36 in which the horizontal axis represents time and the vertical axis represents stiffening provided by the implant 10. Line A is stiffening attributable to the first component 82 (which decays to zero as the first component is absorbed). Line B represents stiffening attributable to the second component (which is at near zero at implantation and increases to a maximum representing a steady-state level of fibrosis). Line C represents stiffening of the soft palate SP which is a sum of the stiffening of lines A and B.

Therefore, with the embodiment of implant 80, immediate post-operative stiffening (and snoring abatement) is achieved. Chronic stiffening is provided by fibrotic response which is permanent. Total stiffening is controlled since the first component 82 is being absorbed as the fibrosis at the second component 84 increases.

Figure 37:
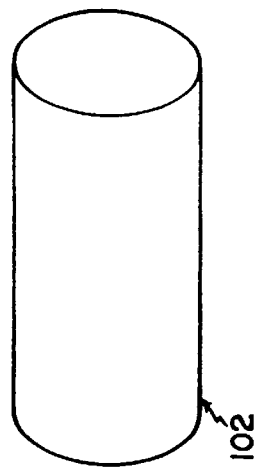
FIG. 37 is a perspective view of an implant for use in the delivery system of FIGS. 38–39.

FIGS. 37–39 show an alternative delivery system 100 for placing an implant in the soft palate SP. FIGS. 37–39 illustrate use of the novel delivery system 100 with a cylindrical implant 102 (such as implant 80 of FIG. 34 or implant). However, the method and apparatus described with reference to FIGS. 37–39 could also be used with other geometries (e.g., the spherical implants of FIG. 7 or rectangular cross-section implants of FIG. 13) as well as an expandable implant as such implant 50 of FIG. 24.

A needle 66' is provided having a ground beveled distal tip 61' for piercing tissue of the soft palate. The needle 66' is hollow and carries the implant 102 in sliding close tolerance. A rod 64' is slidably positioned in the needle 66' proximal to the implant 102. As described above with reference to FIGS. 26–32, the implant 102 is carried by the needle 66' to a desired implant site within the soft palate. At the desired site, the implant 102 is deployed by retracting the needle 66' while holding the rod 64' in place. Relative movement between the rod 64' and needle 66' causes the rod 64' to dispel the implant 102 from the needle 66' without need for moving the implant 102 relative to the soft palate.

While advancing the needle 66' through the soft palate, tissue and body fluids may be inclined to enter the needle 66' and later interfere with discharge of the implant 102 from the needle 66'. The embodiment of FIGS. 26–27 avoids such introduction of tissue and fluids into needle 60 by use of a flap 68 on the distal tip 62 of the needle 66. The embodiment of FIGS. 38–39 provides an alternative technique to prevent admission of tissue into the needle 66'.

In FIGS. 38–39, the needle 66' is provided with a plug 104 at the distal tip 61'. Preferably, the plug 104 is a bio-resorbable material (such as the material of the first component 82 of the implant 80 of FIG. 34.). After placing the plug 104 in the needle 66' at the distal tip 61', the distal tip 61' may be ground to a final bevel resulting in the plug 104 assuming the shape of the distal tip of 61' as shown in FIGS. 38–39.

During discharge, the rod 64' (due to retraction of the needle 66') urges both the plug 104 and implant 102 out of the needle 66'. Since the plug 104 is bio-resorbable, it resorbs into the patient's body over time. The implant 102 provides the therapeutic effect described above with reference to altering the dynamic response of the soft palate.

To avoid the plug 104 being urged proximally into the needle 66', the needle 66' includes a first bore 66a' having a diameter approximate to that of the rod 64' and implant 102 and a second bore 66b' at the distal tip 61'. The second bore 66b' is coaxial with the first bore 66a' and is larger than the first bore 66a' so that an annular retaining edge 65' is defined within the needle 66'. The plug 104 abuts the retaining edge 65' and is restricted from being urged into the needle 66' as the needle 66' is advanced through the tissue of the soft palate. The needle 66' may be porous at the distal tip so the needle with a loaded implant 102 may be soaked for sterilization.

Figure 40:
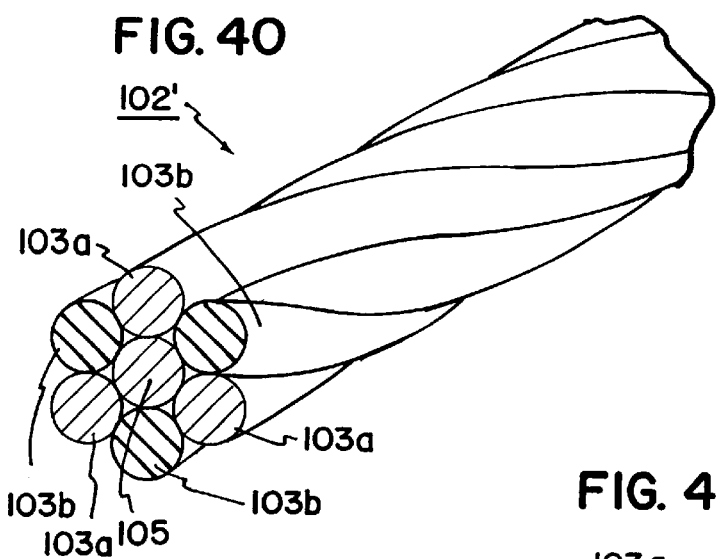
FIG. 40 is a perspective view of a braided implant.
Figure 41:
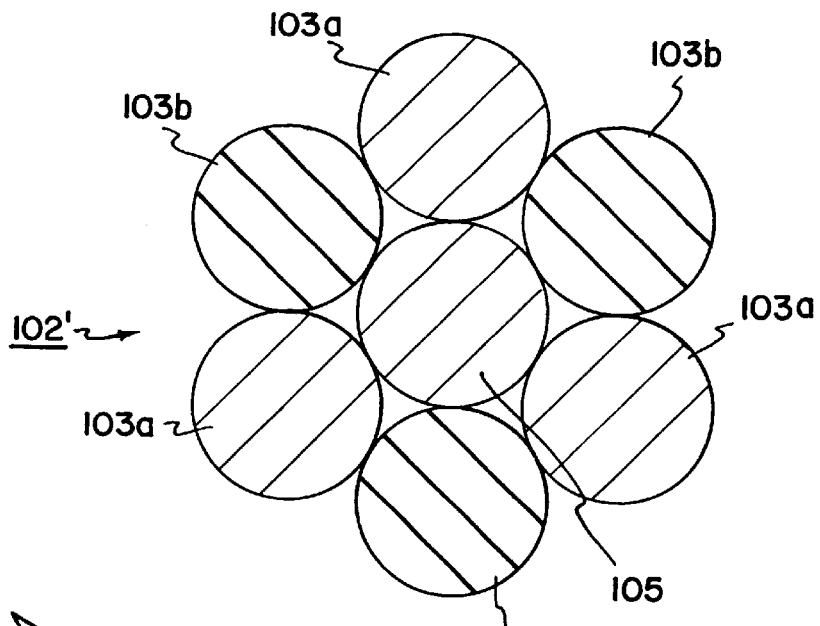
FIG. 41 is an end view of the implant of FIG. 40.

FIGS. 40–41 illustrate an implant 102' formed of twisted or braided fibers 103a, 103b. While a single type fiber could be used, the embodiment is preferably formed of two different fibers 103a, 103b braided or twisted together. One fiber 103a may be provided for encouraging fibrotic response. Such a fiber 103a may be polyester or silk suture material (in which individual fibers 103a may be formed of braided or twisted elements). The other fiber 103*b* may be a bio-resorbable fiber as in FIG. 33 (e.g., bio-resorbable suture material which may include natural materials such as collagen or synthetic materials such as the PDS suture material previously described). Alternatively, the second fiber 103*b* may be a non-resorbable material such as polypropylene suture material to provide added stiffness to the implant. The fibers 103*a*, 103*b* may be bonded together along the axial length of the implant 102' to provide added stiffness.

Figure 42:
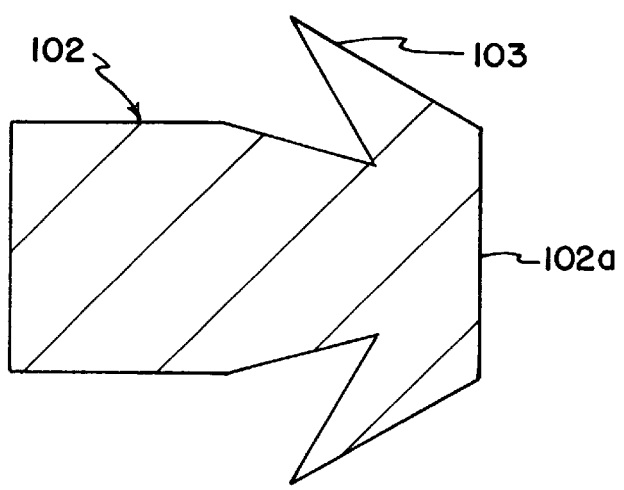
FIG. 42 is a side sectional view of an implant with an anchor.

Referring to FIG. 42 and using implant 102 of FIG. 37 as an example, a distal end 102*a* of the implant 102 (i.e., the first end of the implant 102 to be discharged from needle 66') may be scored or otherwise provided with an anchor 103 to flair outwardly following discharge from the needle 66'. Such flaring aids to anchor the implant 102 in place while tissue in-growth matures. Such flaring can also be provided by radially extending fibers on the implant 102 which are folded down in the needle and which would radially project in the event the implant were to follow the needle 66' during needle retraction.

A braiding operation as described with reference to FIGS. 40–41 provides enhanced design flexibility. Such braiding can incorporate many different types of fibers for various functions. For example, radio-opaque fibers may be provided in the braid to permit visualization of the implant under fluoroscopy. The structure (and flexibility) of the braided implant can be varied by adding a core material to the braid or varying tightness of the braid. FIGS. 40 and 41 show a core or central fiber 105. The central fiber 105 may be the same material as either of fibers 103*a*, 103*b* or may be a different material to add stiffness or other mechanical property. For example, the fibers 103*a*, 103*b* may be non-bio-resorbable while core 105 is resorbable. Core 105 may be metal to add stiffness or be radio-opaque. Core 105 may be a coil or spring-shape core. In the construction of the braided implant 102', all fibers 103*a*, 103*b* and core 105 are preferably co-terminus with the implant 102'. In other words, the ends of the fibers 103*a*, 103*b* and core 105 are positioned at the axial ends of the implant 102'. The ends may be heat treated or otherwise adhered to prevent unraveling of the braided implant 102'.

The foregoing describes numerous embodiments of an invention for an implant for the soft palate to alter a dynamic response of the soft palate. The invention is much less traumatic than prior surgical treatments. Further, the invention permits use of reversible procedures as well as procedures which can be selectively tuned both during surgery and post-operatively. Having described the invention, alternatives and embodiments may occur to one of skill in the art. For example, the strips of FIG. 13 may be encased coiled springs which may be tightened to further stiffen the strips. Such strips may also be hinged segments. Also, the present invention can cover any fibrosis-inducing agent (e.g., polyester fabric, with or without heat application or chemical application—such as ethyl alcohol, or such application in a manner to create a permanent scar with the soft palate) placed into the soft palate to stiffen the soft palate. For example, such chemical may be introduced through incision 70 or a heat source may be inserted through incision 70. The present invention need not be repeated to continue efficacy since the stiffening is permanent. It is intended that such modifications and equivalents shall be included within the scope of the following claims.

What is claimed is:

1. A method for treating snoring of a patient, said method comprising:

providing an implant for altering a dynamic response of a soft palate of the patient to air flow past said soft palate;

implanting said implant into said soft palate to alter said dynamic response;

said providing including selecting an implant formed of a braid of multiple fibers that provide stiffening to said palate resulting at least in part from a fibrotic response of a tissue of the soft palate to the material.

2. A method according to claim 1, wherein the multiple fibers include a bio-resorbable and non-resorbable fiber.

3. A method according to claim 1, wherein the multiple fibers are non-resorbable fibers.

4. A method according to claim 1, wherein said implant is formed of multiple fibers of different materials to provide different stiffening to said palate.

5. An apparatus for treating snoring of a patient suffering from snoring attributable, at in least in part, to a snoring sound generated by oscillation of a soft palate of said patient in response to airflow past said soft palate and where said soft palate has a characteristic dynamic response to said airflow prior to treatment, said apparatus comprising:

an implant of bio-compatible material sized to be embedded within said soft palate; and said implant formed as a braid of multiple fibers that provide stiffening to said palate resulting at least in part from a fibrotic response of a tissue of the soft palate to the material.

6. An apparatus according to claim 5, wherein the multiple fibers include a bio-resorbable and non-resorbable fiber.

7. An apparatus according to claim 5, wherein the multiple fibers are non-resorbable fiber.

8. An apparatus according to claim 5, wherein the multiple fibers are twisted together along a length of the implant with the fibers having terminal ends at opposite ends of the implant.

9. An apparatus according to claim 8, wherein the multiple fibers are of different materials to provide different stiffening to said palate.

10. An apparatus method according to claim 5 wherein said multiple fibers are polyester fibers.

* * * * *